(12) United States Patent
Dendukuri et al.

(10) Patent No.: US 8,647,742 B2
(45) Date of Patent: Feb. 11, 2014

(54) DIAGNOSTIC GEL COMPOSITION, METHOD FOR MAKING A DIAGNOSTIC GEL COMPOSITION

(75) Inventors: Dhananjaya Dendukuri, Bangalore (IN); Reeta Katiyar, Bangalore (IN); Lakshmi P. Sivakumaran, Bangalore (IN)

(73) Assignee: Achira Labs Pvt. Ltd., Bangalore (IN)

( * ) Notice: Subject to any disclaimer, the term of this patent is extended or adjusted under 35 U.S.C. 154(b) by 0 days.

(21) Appl. No.: 13/504,038

(22) PCT Filed: Dec. 28, 2009

(86) PCT No.: PCT/IB2009/055967
§ 371 (c)(1), (2), (4) Date: Apr. 25, 2012

(87) PCT Pub. No.: WO2011/080537
PCT Pub. Date: Jul. 7, 2011

(65) Prior Publication Data
US 2012/0258309 A1   Oct. 11, 2012

(51) Int. Cl.
*B32B 5/16* (2006.01)

(52) U.S. Cl.
USPC ............ 428/402; 428/407; 424/9.6; 424/501; 522/6; 522/153; 252/301.35; 106/316

(58) Field of Classification Search
USPC ........ 428/402–407; 424/9.6, 501; 522/6, 153; 252/301.35; 106/316
See application file for complete search history.

(56) References Cited

U.S. PATENT DOCUMENTS

| 5,300,779 A | 4/1994 | Hillman et al. |
| 2007/0105972 A1 * | 5/2007 | Doyle et al. ...................... 522/1 |
| 2010/0092393 A1 * | 4/2010 | Haghgooie et al. ............ 424/9.6 |

FOREIGN PATENT DOCUMENTS

| EP | 0803288 | | 3/2003 |
| WO | WO 2009/061392 | | 5/2009 |
| WO | WO2009/061392 | * | 5/2009 |
| WO | WO 2011/080537 | | 7/2011 |
| WO | WO2011/080537 | * | 7/2011 |
| WO | WO 2011/080538 | | 7/2011 |
| WO | WO 2011/080539 | | 7/2011 |

OTHER PUBLICATIONS

Honda Masaki et al: "Confined stimuli-responsive polymer gel . . . " Langmuir: The ACS Journal of Surfaces and Colloids Jul. 21, 2009, pp. 8349-8356.*
Brown, X. Q. et al. "Evaluation of polydimethylsiloxane scaffolds with physiologically-relevant elastic moduli: interplay of substrate mechanics and surface chemistry effects on vascular smooth muscle cell response," *J. Biomaterials*, vol. 26, No. 16, pp. 3123-3129, Jun. 1, 2005.
Dendukuri, D., et al., "Continuous-flow lithography for high-throughput microparticle synthesis," *Nat Mater*, 5(5): p 365-369, 2006.
Jang, J. et al. "A route to three-dimensional structures in a microfluidic device: stop-flow interference lithography," *Angewandte Chemie*, vol, 46, No. 47, pp. 9027-9031, 2007.
Meagher, R. J. et al. "An integrated microfluidic platform for sensitive and rapid detection of biological toxins," *Lab on a Chip*, vol. 8, No. 12, pp. 2046-2053, 2008.

* cited by examiner

*Primary Examiner* — Leszek Kiliman
(74) *Attorney, Agent, or Firm* — Levine Bagade Han LLP

(57) ABSTRACT

The invention relates to a diagnostic gel composition for use as a diagnostic element in diagnostic devices. The diagnostic gel composition is derived from a compound having a formula D-Sp-Po wherein D is a diagnostic group; Sp is a hydrophilic spacer group; and Po is a polymerizable group. The diagnostic gel composition of the invention has dimensions ranging from about 250 nanometers to about 1000 micrometers, and a Young's modulus ranging from about 10 kilopascals to about 200 kilopascals. The invention also provides method for making the diagnostic gel composition. The method comprises providing a composition comprising a porogen, an initiator and a compound having a formula D-Sp-Po; polymerizing the composition to form a polymerized composition; and washing the polymerized composition to form the diagnostic gel composition.

19 Claims, 14 Drawing Sheets

104

106

DIAGNOSTIC GEL COMPOSITION, METHOD FOR MAKING A DIAGNOSTIC GEL COMPOSITION

CROSS-REFERENCE TO RELATED APPLICATIONS

This application is a U.S. National Phase under 35 U.S.C. 371 to PCT International Patent Application No. PCT/IB2009/055967 filed on Dec. 28, 2009, the content of which is incorporated herein by reference in its entirety.

TECHNICAL FIELD

The invention relates generally to a diagnostic gel composition for a diagnostic element that is useful in the development and manufacture of a microfluidic chip-based platform to perform rapid disease detection and more specifically to perform immunoassays on chip.

BACKGROUND

The detection of analytes including proteins, DNA/RNA and metabolites from body fluids and other samples of biological origin is essential for a variety of applications including medical testing, toxin detection and forensic analysis. Improved, point-of-care testing of such analytes is an urgent worldwide requirement. The current systems designed for such applications suffer from several drawbacks such as high costs, bulkiness and delayed results. There is therefore a large unmet need for the development of systems that are low-cost, portable, convenient to handle and show high efficiency towards detection. These systems should also be capable of rapidly identifying a broad range of analytes from samples of biological origin. Microfluidic, lab-on-a-chip methods have gained prominence over the past decade as solutions to this problem. The measurement of proteins using microfluidic immunoassays has been one of the important focus areas. While microfluidic technologies have gained prominence as a solution to such problems, many of them are handicapped by the absence of mature manufacturing capabilities that can enable the transition of ideas from academic labs to industry. They typically use lab-scale fabrication techniques and materials that are incompatible with standard industrial processes, which are also not conducive for scaling up for the rapid production of many devices.[1] All the components of a device need to be developed and adapted for making a device that meets the requirements as delineated herein.

BRIEF DESCRIPTION

In one aspect, the invention provides a diagnostic gel composition. The diagnostic gel composition of the invention has dimensions ranging from about 250 nanometers to about 1000 micrometers, and a Young's modulus ranging from about 10 kilopascals to about 200 kilopascals. The diagnostic gel composition is derived from a compound having a formula D-Sp-Po;

wherein D is a diagnostic group; Sp is a hydrophilic spacer group; and Po is a polymerizable group.

In another aspect, the invention provides a method for making a diagnostic gel composition. The method comprises providing a composition comprising a porogen, an initiator and a compound having a formula D-Sp-Po; polymerizing the composition to form a polymerized composition; washing the polymerized composition to form the diagnostic gel composition.

In further aspects, the invention provides a diagnostic element comprising a diagnostic gel composition of the invention.

In yet another aspect, the invention provides a diagnostic device comprising the diagnostic element that comprises the diagnostic gel composition of the invention.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
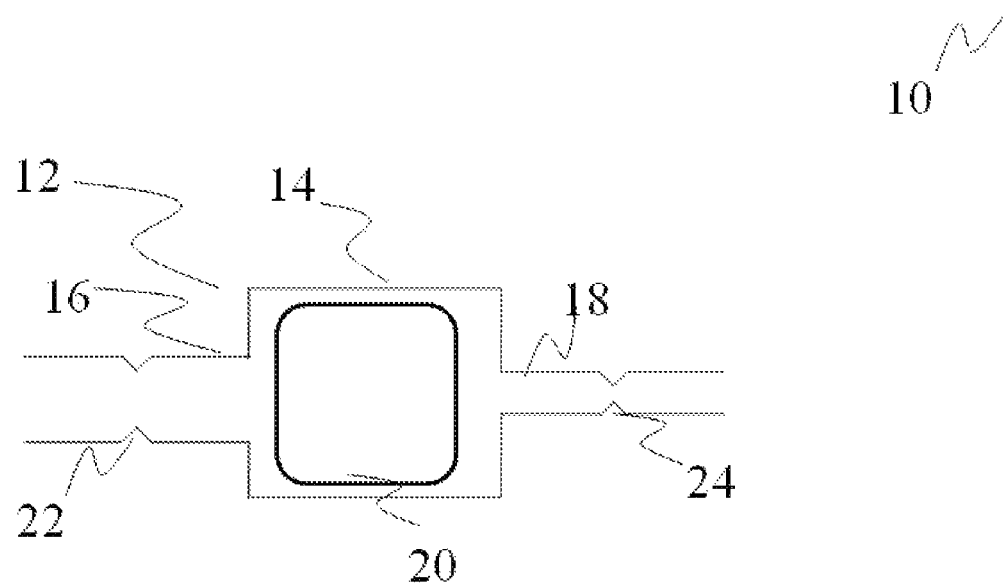
FIG. 1 is a diagrammatic representation of an exemplary diagnostic element according to one aspect of the invention.

As used herein and in the claims, the singular forms "a," "an," and "the" include the plural reference unless the context clearly indicates otherwise.

It should be noted that in the detailed description that follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

In one aspect, the invention provides a diagnostic element and a diagnostic device comprising the diagnostic element. The diagnostic device of the invention may also be referred to as the diagnostic chip or simply as a chip by one of ordinary skill in the art. The diagnostic element of the invention is shown in FIG. 1 and is represented by the numeral 10. The diagnostic element comprises a shaped channel, generally depicted by the numeral 12 in FIG. 1. The shaped channel comprises at least one holding port 14. The holding port is shown in a rectangular two-dimensional representation, but it may be of any shape, such as, but not limited to, trapezoidal, square, cylindrical, cubical, and the like, and combinations of shapes as well. The shaped channel further comprises an inlet passage 16 and an outlet passage 18. The inlet passage allows the flow of fluids and other materials for the invention into the holding port and the outlet passage allows the flow of fluids out into a suitable reservoir or a collector. The ratio of the widths of the outlet and inlet passage can be varied to hold the diagnostic gel securely within the holding port. The shaped channel of the invention is generally made of a material that is suitable for the intended purpose, as will be described later.

The diagnostic element of the invention also comprises a diagnostic gel 20. A typical diagnostic gel useful in the invention may be derived from a composition comprising a compound having a formula:

D-Sp-Po;

wherein D is a diagnostic group;
Sp is a hydrophilic spacer group; and
Po is a polymerizable group.

The compound used to make the diagnostic gel of the invention comprises a polymerizable group. A polymerizable group, as used herein, means any chemical entity that is capable of reacting with a complementary chemical entity to form a chain of linkages, known in the art as a repeat unit. An example of a polymerizable group is a vinyl group, represented by a double bond between two carbon atoms. This group can react with another vinyl group to form a carbon-carbon chain. Another exemplary polymerizable group is an epoxy group, which can react with another epoxy group to form alkoxy chain. Polymerizable group as used herein is also meant to include more than one chemical entity. Thus, one compound may have more than one vinyl group. When a plurality of such chemical entities is present, then a crosslinked network results when polymerized. This is especially advantageous in the invention. In one exemplary embodiment, the composition used to make the diagnostic gel of the invention may comprise a first compound having only one polymerizable group and a second compound having more than one polymerizable group, in a weight ratio of 90:10 respectively. In another exemplary embodiment, the weight ratio of the first and second compound 50: 50, while in yet another exemplary embodiment, the weight ratio may be 0:100 respectively. In some other exemplary embodiments, a polymerizable group may be a dicarboxylic group. This group may react with, for example, a dialcohol group to form a polyester. In this situation, the chemical entity being considered is a carboxylic acid group, and the complementary chemical entity is a alcohol. Similarly, a dicarboxylic acid and a diamine could be used to form a diamine. Other exemplary polymeric moieties include polyurethanes, polyacetals, polyethers, and the like. In the situation of, for example, a dicarboxylic acid and a dialcohol, it may be useful to include a compound having tricarboxylic acid or a trialcohol or both in the mixture to form the compound from which a diagnostic gel is derived. In this case, about 10 weight percent of the triacarboxylic acid with respect to the dicarboxylic acid may be present.

The compound useful in the invention also comprises a hydrophilic spacer group, represented in the formula as Sp. Typical hydrophilic groups useful in the invention include, but not limited to, ethers, alcohols, glycols, amines, esters, amides, alcohols, carboxylic acids, and the like. These groups must be present in the final diagnostic gel composition, and hence must not undergo any chemical transformation during the diagnostic gel formation step, or if they do undergo chemical transformation, they must transform to another hydrophilic group. Hydrophilic group, as used herein, means any group that is capable of absorbing water. Another way of describing hydrophilic group is that those groups that when exposed to a drop of water, the contact angle between the water and the surface of the material tends to be an acute angle. A particularly useful spacer group is an ether group.

The compound further comprises at least one diagnostic end. Diagnostic end, as used herein, means any chemical moiety that may be used for the detection of certain other moieties. For example, diagnostic end could mean antibodies that are used to detect specific types of cells or antigens.

The diagnostic gel is formed from the composition described herein. In one exemplary embodiment, the diagnostic gel is formed by curing a composition of the invention having 90 weight percent a compound having a single polymerizable group, a spacer group, and a diagnostic end, and 10 weight percent a compound having two polymerizable groups, by the exposure to light to form a structure having a three-dimensional architecture, wherein the dimensions are in the range of about 100 nm to about 1000 microns. Dimensions may include, length, breadth, height, volume, area, circumference, perimeter, and the like, and the choice of dimension depends on the shape of the architecture. One such method of forming a diagnostic gel is given in US2007/0105972A1.

The composition useful in the invention to make the diagnostic gel also includes a porogen. Porogens are external compounds that are added to the composition to induce pores into the composition having definite characteristics, such as pore size, pore density, and the like, and combinations thereof. A useful porogen is a compound that has the ability to create a pore with a definite size that ranges from 5 nanometers to about 1000 nanometers. In one embodiment, the porogen is sodium bicarbonate, while in another embodiment, the porogen is sodium chloride, and in yet another embodiment, it is citric acid. In some embodiments, the porogen is a liquid composition that is dispersed through the composition used to make the diagnostic gel. Some examples include, but are not limited to, acetic acid, poly(ethylene glycol)-200, ethylene glycol, glycerol, and the like. In yet other embodiments, the porogen is a gaseous fluid such as carbon dioxide. Such gaseous fluids may be produced in situ using appropriate compounds such as sodium carbonate, sodium bicarbonate, calcium carbonate, and the like. In some other embodiments, the gaseous fluid may be trapped inside the composition through appropriate means, such as adsorption.

The porogen may be allowed to remain within the composition of the invention, as long as it is known that the porogen will not affect the performance of the diagnostic gel. In such instances, the diagnostic gel comprises the porogen as well. Alternately, the porogen may be washed off in a step to provide the diagnostic gel. The choice of the porogen and the compound, and the steps involved in the production of the diagnostic gel will determine whether the porogen is allowed to remain or is removed or is washed off in an independent step to form the diagnostic gel of the invention.

The composition of the invention may further include initiators to initiate the polymerization reaction, catalysts, chain transfer agents, retarders, inhibitors, additives to provide strength or improve gelling ability, for example, and other useful components.

The diagnostic gel of the invention is formed by curing the composition described herein. Curing as used herein means the polymerization of the at least one polymerizable group. One skilled in the art will understand that polymerization of the composition may result in a linear polymer, or branched polymer, or a crosslinked polymer network depending on the nature of the composition of the invention. In one embodiment, the curing of the composition of the invention results in a crosslinked polymer network, which when exposed to a suitable solvent will form a crosslinked gel. Curing may be advantageously effected by a photolytic method, which involves exposing the composition to a light of suitable wavelength. In one exemplary embodiment, the composition is present in a liquid form, and is flowed into a suitable container. In a specific embodiment, the container is the holding port of the diagnostic element. In another specific embodiment, the container is a separate part of a diagnostic device, such as a preparation port, as described herein. In yet another specific embodiment, the container is a distinct gel formation device that is available independently of the diagnostic device of the invention, and the diagnostic gel formed therefrom is collected separately and used in the diagnostic element. Curing is typically effected by the exposure of the composition through a shaped mask for a predetermined period of time in order to cure only the exposed parts of the composition. The light used for effecting cure is typically ultraviolet radiation, typically having a specific wavelength, amplitude and intensity, but other radiations such as gamma radiation may also be used to cure the compound to form the diagnostic gel. The time needed for effecting curing depends on the nature of the compound, the amount of photoinitiator, etc., and may range from about 0.5 seconds to about 30 seconds. Subsequently, the diagnostic gel is washed with a suitable solvent or solvent mixture to wash off the uncured portion of the composition from the diagnostic gel.

In another embodiment, a monomer having at least one polymerizable group is partially cured by partial exposure to light. The partial curing may be effected by exposure of the monomer to light source for shorter period of time than necessary for complete curing, for example less than 3 seconds. Alternately, partial curing may also be effected by exposure of the monomer to a light having a different intensity from the light used for the complete curing. Further, incomplete curing may also be effected by the use of lower concentration of photoinitiator with respect to the concentration of monomer. Subsequently, the compound of the invention is flowed in, along with a compound that contains a diagnostic end and a polymerizable end. Complete curing of the mix is effected by further exposure of the composition of the invention to the light source optionally through a shaped mask for a predetermined period of time. This results in the diagnostic end being added to the surface of the diagnostic gel. The final cured product may then be subjected to a washing step as necessary.

Alternately, a composition comprising a polymerizable end and a first reactive group may be cured to form a polymerized material that comprises a reactive group. This polymerized material may then be reacted with a diagnostic molecule that comprises a diagnostic end and a co-reactive group that is capable of reacting with the reactive group on the polymerized material. The reaction between the reactive group on the polymerized material and the diagnostic molecule will result in the diagnostic gel of the invention. In one exemplary embodiment, the reactive group on the polymerized material is a maleimide group and the c-reactive group on the diagnostic molecule is a sulfhydryl group.

The composition of the invention already may possess pores contained within it. These pores may also be referred to as void volume or holes by one skilled in the art. These pores are generally taken as the average distance between two crosslinking points. The washing step may also wash off the porogen from the diagnostic gel to leave behind pores within the diagnostic gel. The size of the pore will correspond directly to the size of the porogen that was present before the washing off step. Alternately, the porogen may be allowed to stay within the diagnostic gel of the invention, while still forming pores within the diagnostic gel. In yet another embodiment, interference patterns from different light sources may be used to induce pores in the diagnostic composition of the invention, as described in Jang et al., Angew Chem. 2007. This technique obviates the need for a porogen in the composition.

The diagnostic gel formed has a dimension that ranges from about 250 nanometers to about 1000 micrometers. Dimensions as used herein, means any of the standard measurement characteristic of a given geometric shape, and may include, but not limited to, length, breadth, height, diagonal length, circumference, diameter, radius, or combinations thereof. The diagnostic gel is also characterized by a pore size. The pore size most useful in the invention generally ranges from about 5 nanometers to about 1000 nanometers. The diagnostic gel of the invention is also characterized by a Young's modulus. Methods for measuring Young's modulus are known one in the art, and one exemplary instrument used for measuring Young's moduus is Universal Testing Machine, which uses the plot between Stress-Strain to estimate the Young's modulus.

As stated earlier, the diagnostic gel may be formed in a previous step, which is then collected and purified separately, chemically modified and then introduced into the shaped channel by flowing with a suitable flow fluid. In a further alternate embodiment, the diagnostic gel may be formed in a separate section of the shaped channel and subsequently, flowed into the holding port. In yet another embodiment, the composition is flowed into the holding port and the diagnostic gel is formed in the holding port using the methods described herein. The flowing of the composition of the invention may be effected by suitable flowing methods known to those skilled in the art. Alternately, droplets of the composition of the invention are formed by flowing the composition into an already flowing immiscible secondary liquid, wherein the composition is flowed into the secondary liquid at a right angle relative to the flow direction of the secondary liquid. Without being bound by any theory, the size and shape of the droplet is generally known to depend on the viscosity of the composition, the shear rate posed by the secondary liquid, channel geometry, and other factors. These droplets may then be cured in the holding port or in a separate section of the shaped channel. Several factors are taken into account to ensure that the diagnostic gel or the composition of the invention is encapsulated within the holding port. Without being bound to any theory, the ability of the diagnostic gel or the composition of the invention to be flowed and encapsulated into a holding port is proportional to: the size of the diagnostic gel; the Young's modulus of the diagnostic gel or the composition; viscosity of the fluid flow; flow rate of the fluid flowing; Young's modulus of the material forming the shaped channel; temperature; dimensions of the inlet passage; dimensions of the outlet passage; compressibility factor of the diagnostic gel or the composition; pressure, such as vacuum at a given surface area; and the like. There may be other factors affecting the ability of the diagnostic gel or the composition to be flowed into the holding port and encapsulated therein.

Figure 8:
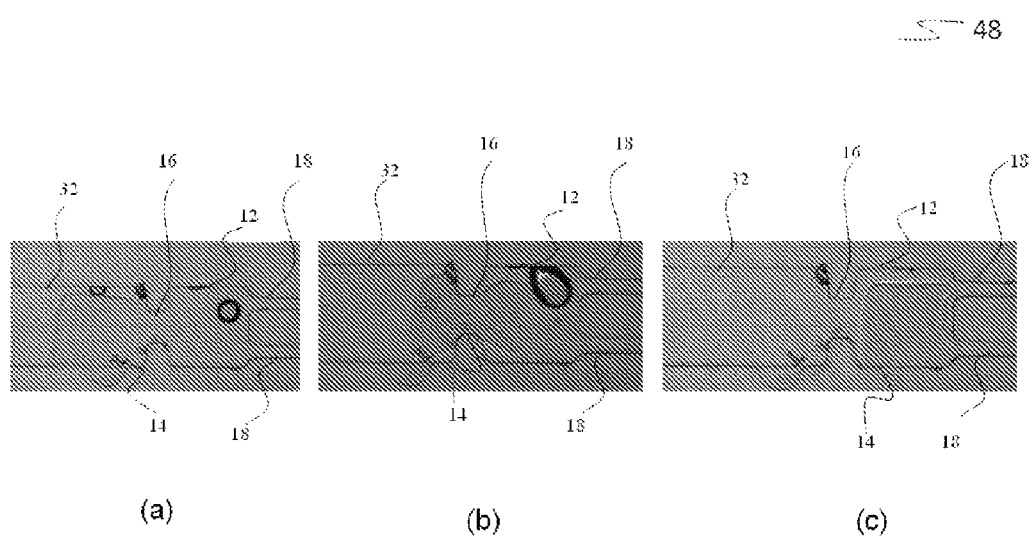
FIG. 8 is photographic representations of results of the process as explained in FIG. 7 showing the capturing the diagnostic gel of the invention in the holding port.

Thus, in one embodiment, the shaped channel is made of soft material having low Young's modulus and the diagnostic gel is very hard. An example of a soft material that may be used to make the shaped channel is PDMS. During flow in this situation, the soft shaped channel deforms to allow flow of the diagnostic gel into the holding port. In another embodiment, the shaped channel is made of a rigid hard material. An example of a hard rigid material may be poly(methyl methacrylate), that is commercially available under a variety of trade names such as Plexiglass®, Gavrieli®, Vitroflex®, Limacryl®, R-Cast®, Per-Clax®, Perspex®, Plazcryl®, Acrylex®, Acrylite®, Acrylplast®, Altuglas®, Polycast®, Oroglass®, Optix® and Lucite®. Another useful material for this application is a cyclic olefin copolymer, commercially available as, for example, Topas® from Polyplastics. In this situation, a positive pressure or negative pressure may be used to push or pull the diagnostic gel through a channel containing a holding port. Negative pressure may be achieved by applying vacuum at a desired location. Further, in such instances, the diagnostic gel is soft enough such that it can deform while passing through the inlet passage into the holding port and be encapsulated within (FIG. 8). The gel is prevented from flowing out of the holding port in the direction of flow by use of appropriate constricting geometry where the inlet passage width is greater than the outlet passage width.

In one embodiment, the useful values of the Young's modulus for the diagnostic gel of the invention ranges from about 1 kPa to about 200 kPa. An exemplary diagnostic gel may be one derived from poly(ethylene glycol)-diacrylate that has insulin antibodies attached to it. In another exemplary embodiment, the diagnostic gel may be a poly(ethylene glycol) diacrylate derived gel with antigen to the antibodies that are generated upon exposure to the HIV virus.

In some embodiments, the diagnostic gel is held within a certain location by the appropriate use of positive and negative pressure. A positive pressure may be used to force the flow through a channel, while a negative pressure may be used to retard the flow through a channel. Negative pressure may be achieved by applying vacuum at a desired location. Thus, the diagnostic gel may be flowed through the channel and then held in a certain desired location by applying vacuum at that location through the walls of the channel. This would also imply that the walls of the channel are made of a material amenable to the application of vacuum through it, while simultaneously being impermeable to the fluids flowing through it.

Turning back to the FIG. 1, the diagnostic element of the invention further comprises a first recess 22 on the inlet passage and a second recess 24 located on the outlet passage. The first and second recesses are located in such a way that the holding port is situated in between the two recesses. The recesses are provided so that it facilitates the removal of the holding port alone leaving the inlet passage and the outlet passage intact. The holding port which contains the diagnostic gel and has been removed at the recesses can then be used for a variety of diagnostic purposes. In one exemplary embodiment, the diagnostic gel is subjected to a microscopic observation to determine presence or absence of certain microscopically visible particles. In other exemplary embodiment, the diagnostic gel is subjected to a predetermined extraction method step to extract any extraneous particles attached to the diagnostic end. In yet another exemplary embodiment, the diagnostic gel is subjected to a radiation of suitable wavelength and known intensity and amplitude for quantification purposes.

In one embodiment, the diagnostic element of the invention may comprise more than one diagnostic gel. Each diagnostic gel has a distinct diagnostic end that is used for a specific purpose of identifying one particular moiety. Each diagnostic gel may have other aspects of the composition, such as the spacer group and the polymerizable group the same or different. One skilled in the art will be able to choose the appropriate combination of the components involved in the composition to make the diagnostic gel without great undue experimentation. Presence of multiple diagnostic gels will allow for multiple examinations and diagnosis using a single chip, thus greatly reducing time and effort involved. In another embodiment, the diagnostic element of the invention may comprise a diagnostic gel that comprises spatially segregated diagnostic ends, wherein each diagnostic end may be the same or different. Techniques to make such diagnostic gels are known in the art, for example,(FIG. 4 in [2]) Dendukuri, D., Pregibon, D. C., Collins, J., Hatton, T. A. and Doyle, P. S. "Continuous Flow Lithography for High-Throughput Microparticle Synthesis", Nat. Mater., 5, 365-369, May 2006.

Figure 2:
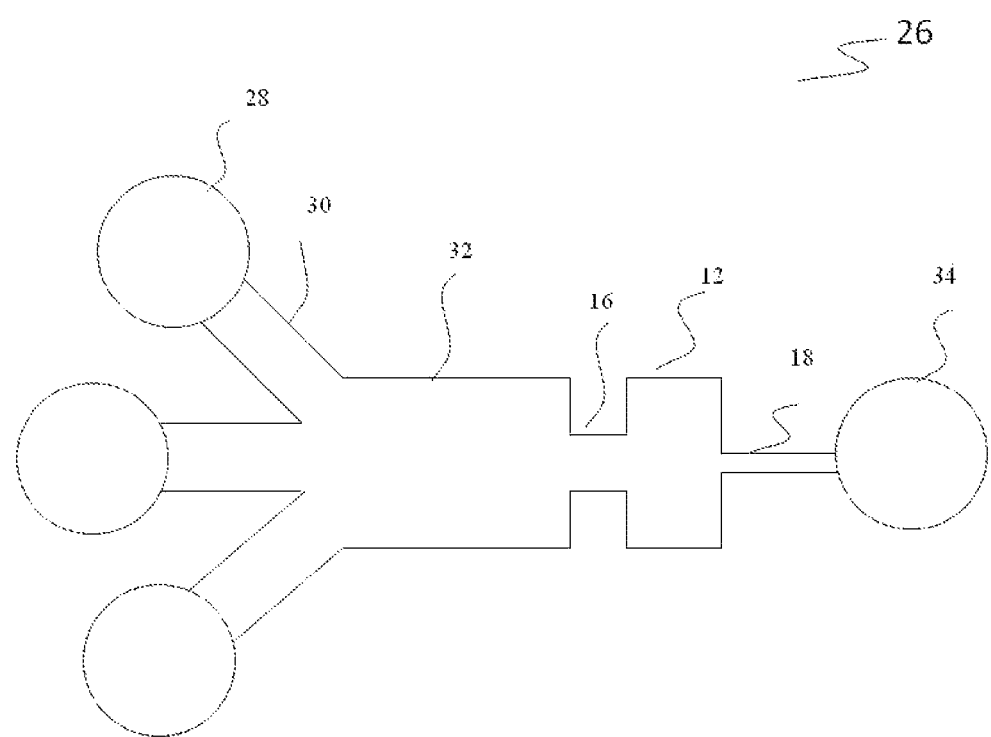
FIG. 2 is a diagrammatic representation of an exemplary diagnostic device according to another aspect of the invention.

FIG. 2 shows a diagnostic device of the invention 26. The diagnostic device comprises at least one holding port 12, the inlet passage 16 and the outlet passage 18. For convenience sake, only holding port is shown here for visual purposes and the diagnostic gel 14 is not shown here. Similarly, the first recess 22 and second recess 24 are not shown here, however they may also be present in the diagnostic device of the invention. The diagnostic device also comprises at least one inlet port 28. The inlet port may be a reservoir for the introduction of suitable fluids into the device. Fluids useful in the device may include any of the solvents that are used for separation and identification. The fluid is also sometimes referred to in the art as mobile phase. In one embodiment, the fluid introduced into the device may be a phosphate buffer. The device also comprises a sample introduction port, through which samples to be analyzed are introduced into the device. The inlet port may be used as the sample introduction port or a separate port may be used for the purpose based on the intended application of the diagnostic device. Samples containing entities of interest, also known as analytes in the art, are typically introduced into the device as a solution in the mobile phase, usually wherein the sample is of an unknown concentration. In some embodiments, one or more of the inlet ports may also serve as a sample introduction port for the suitable introduction of samples into the diagnostic device. Typical method for introduction of sample includes injection of a solution of the sample. As shown in FIG. 2, more than one inlet ports may be present for a given device. The device may be capable of utilizing only the number of inlet ports necessary for a given application while sealing the other inlet ports off from the rest of the device to ensure that the operation of the device proceeds smoothly.

The device then comprises an inlet arm 30 that connects the inlet port to the rest of the device. Each inlet port is associated with an inlet arm. The device then comprises a preparation port 32. The preparation port may have many functions that depend on the final application. In one exemplary embodiment, the preparation port agitates the mobile fluids for better mixing of the fluids coming from various inlet ports. In another exemplary embodiment, the preparation port is used to degas the mobile phase. In another exemplary embodiment, the preparation port may be used to filter out cells or other particles exceeding a threshold size of 1 micron from the sample. The device then comprises an outlet port 34 which is linked to the outlet passage. The outlet port may be a sink for disposal of waste, or it is a reservoir to collect all the fluids passed through the device.

The fluids are generally flowed into the device through methods known in the art. In a typical embodiment, the fluid is pumped into the device using a metering pump with controllable flow rates. In another embodiment, a suction pressure is applied on the outlet port side of the device, which allows for the flow of the fluid. In other embodiments, electromagnetic force is applied at a particular point on the device, which makes the flow possible. Other methods used to effect flow of fluids include, but not limited to capillary flow, acoustically driven flow, centrifugally driven flow, piezoelectric pump, and the like. In one exemplary embodiment, the diagnostic gel of the invention is forced into the holding port at a high pressure, and then held inside the holding port using lower pressures than the pressure at which it is flowed in. This enables the diagnostic gel to be firmly ensconced within the holding port during operation.

In one illustrative embodiment, when the device is in its functional state, it comprises one inlet port through which the sample is pumped into the device at a predetermined flow rate. The sample passes through the inlet arm and is then subsequently filtered in the preparative port. The sample then passes through a first holding part that contains a diagnostic gel or other absorbent material such as polysaccharide-based materials containing physically encapsulated, fluorescently-labeled detection antibodies inside it. These antibodies bind to a specific analyte such as HIV-virus induced antibodies present in the sample, forming a complex which is then leached out of the diagnostic gel, and then transported downstream to the second diagnostic gel. The second diagnostic gel contains chemically bound primary antibody species on its surface, also specific to the analyte of interest. A tertiary complex of Primary antibody—analyte—Secondary antibody is then formed at the location of the second diagnostic gel. The remaining portion of the analyte then flows out through the outlet passage into the outlet port. The presence and concentration of the analyte of interest may be inferred by examining the fluorescent signal emitted from the tertiary complex. In one exemplary embodiment, the diagnostic element that comprises the diagnostic gel with the adsorbed parts of the analyte is then cut at the first and second recesses. This cut diagnostic element is then subjected to an analysis to determine the nature and extent of disease spread, for example. In another exemplary embodiment, a diagnostic tool, such as a microscope, is used to analyze the diagnostic element that is present as a part of the diagnostic device, wherein the diagnostic tool is brought within a suitable distance from the diagnostic element to effect a proper diagnosis.

In a variation to the illustrative embodiment described above, the diagnostic part of the diagnostic gel of the invention that is now adsorbed to the analyte is now separated from the original diagnostic gel by flowing it out using a suitable solvent mixture, and then flowed into a subsequent holding port that comprises a different diagnostic gel, which has a different diagnostic end that can adsorb the first diagnostic end which comprises the analyte to form a second diagnostic element. The second diagnostic element is then used for the diagnosis.

Figure 3:
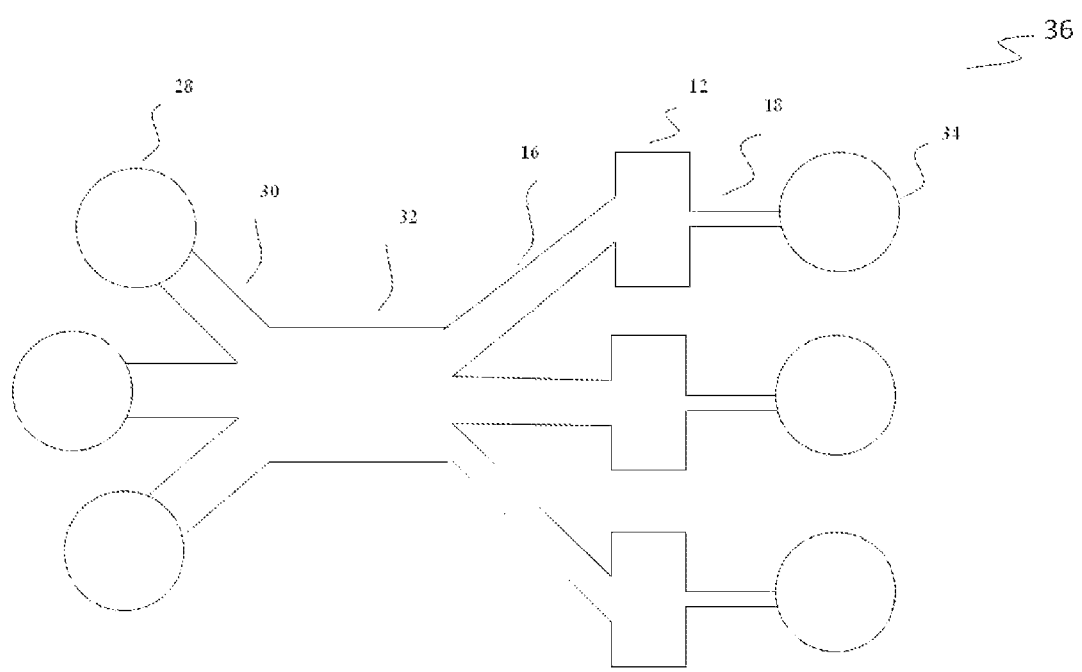
FIG. 3 is a diagrammatic representation of another exemplary diagnostic device with more than one holding port according to one aspect of the invention.
Figure 4:
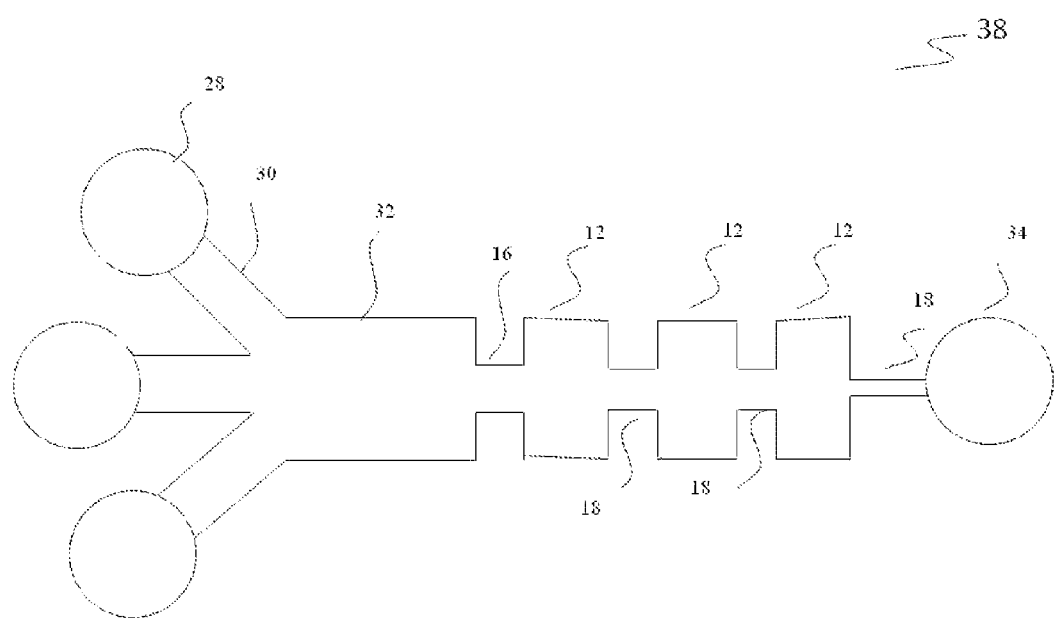
FIG. 4 is a diagrammatic representation of another exemplary diagnostic device where the holding ports are connected in series.

FIG. 3 shows an exemplary diagnostic device of the invention which comprises more than one holding port, each of them depicted by the numeral 12, each holding port associated with its own inlet passage 16 and outlet passage 18. In this particular embodiment, the holding ports are connected in parallel to each other. The mobile phase is flowed into each holding port using appropriate means, such as by using suction or applying vacuum at certain points to ensure flow into the required holding port. FIG. 4 shows another exemplary diagnostic device of the invention wherein the device comprises more than one holding port, and wherein each of the holding port is connected to the other in series. For the sake of convenience, both FIG. 3 and FIG. 4 does not show the diagnostic gel contained within the holding port.

Figures 5, 6:
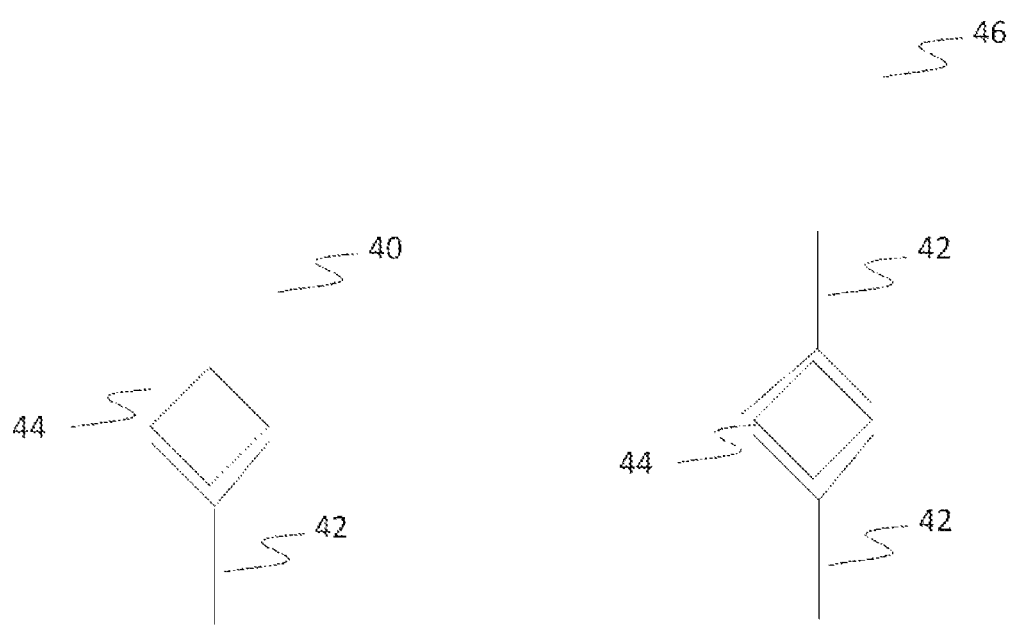
FIG. 5 is a diagrammatic representation showing attachment of an analyte to a diagnostic end of a diagnostic gel according to one aspect of the invention.
FIG. 6 is a diagrammatic representation showing two diagnostic ends for holding the analyte according to another aspect of the invention.

FIG. 5 shows a simplistic visualization of the manner in which the diagnostic gel functions, as represented by the numeral 40. The diagnostic gel comprises a diagnostic end 42, to which a suitable analyte 44 is attached. The diagnostic end is selected such that it is selective and specific to one type of analyte. Thus, a mobile phase comprising anything other than the analyte passes through and around the diagnostic end, while the specific analyte is held by the diagnostic gel. FIG. 6 shows another visualization 46 of the manner in which two different diagnostic gels 42 are used to hold an analyte 44 in place. A typical exemplary situation that utilizes such a visualization is the sandwich ELISA, wherein the analyte is held in place between two different complementary diagnostic ends. Such a form of analysis may be performed advantageously using the diagnostic device of the invention that comprises more than one holding ports, wherein the holding ports are arranged in a serial manner. Other known techniques, as exemplified by the ELISA technique, that may be performed using the diagnostic device of the invention includes Competitive ELISA, Sandwich ELISA, chemiluminescent immunoassay, PCR amplified ELISA, ELONA (enzyme linked oligonucleotide assay), DNA microarray and the like.

Detection of the diagnostic gel which has the analyte linked to it may be achieved through appropriate techniques known in the art. Standard techniques include, but not limited to, optical microscope, fluorescence, chemiluminescence, electrophosphorescence, potentiometry, colorimetry, absorbance, surface Plasmon resonance and the like, and combinations thereof.

Figure 7:
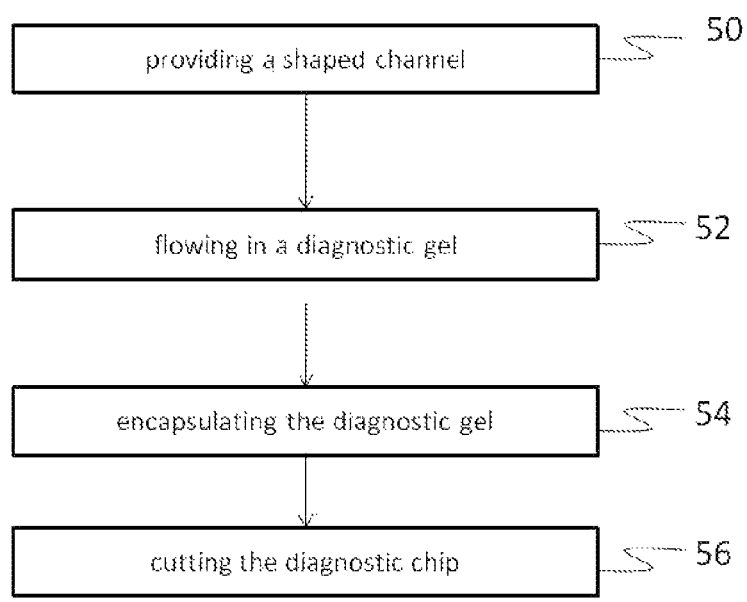
FIG. 7 is a flowchart representation of exemplary steps for a method for making the diagnostic element.

In another aspect, the invention provides a method of making a diagnostic element. The method steps involved in the making of the diagnostic element is shown in FIG. 7 and is generally depicted by the numeral 48. The method comprises a step of providing a shaped channel 50. The method further comprises the step of flowing in a diagnostic gel 52 through the inlet passage into the holding port. The flowing may be effected by the pumping of a fluid, such as a mobile phase, at a predetermined flow rate so as to employ suitable pressure onto the diagnostic gel such that it can squeeze through the inlet passage and into the holding port, but not through the outlet passage. Thus, the diagnostic gel is encapsulated in the holding port as shown in step 54. In an alternate embodiment, the diagnostic gel is formed within the holding port, and subsequently, a fluid is flowed into the holding port to wash off all the extraneous components not associated with the diagnostic gel. The washing step may also induce swelling of the diagnostic gel to its maximum capacity to enable better functioning of the diagnostic gel. In an alternate embodiment, the diagnostic gel is flowed into the holding port and subsequently, it is held in place within the holding port through the appropriate use of vacuum applied against the walls of the holding port. After the diagnostic element comprising the diagnostic gel is subjected to an analyte, the diagnostic element may be cut out, as shown in step 56. The cutting may take place at the first and second recesses. Alternately, the diagnostic element is cut only at the first recess, thus removing the diagnostic element along with the outlet passage and wherever applicable, the outlet port and other parts.

FIG. 8 shows images taken during the process of capturing a diagnostic gel of the invention in the holding port using the method of the invention. FIG. 8(a) shows the diagnostic gel 14 in the preparation port 32 before entry into holding port 12 through the inlet passage 16. FIG. 8(b) shows the diagnostic gel 14 being squeezed into the holding port 12 through the inlet passage 16. In this particular instance, the diagnostic gel is being forced into the holding port through the use of flow of a mobile phase at a suitable flow rate. FIG. 8(c) shows the diagnostic gel 14 that is now trapped in the holding port 12. The diagnostic gel is not allowed to pass into the outlet passages 18 as the dimensions of the outlet passages are such that it is not conducive for passage of the diagnostic gel.

Figure 9:
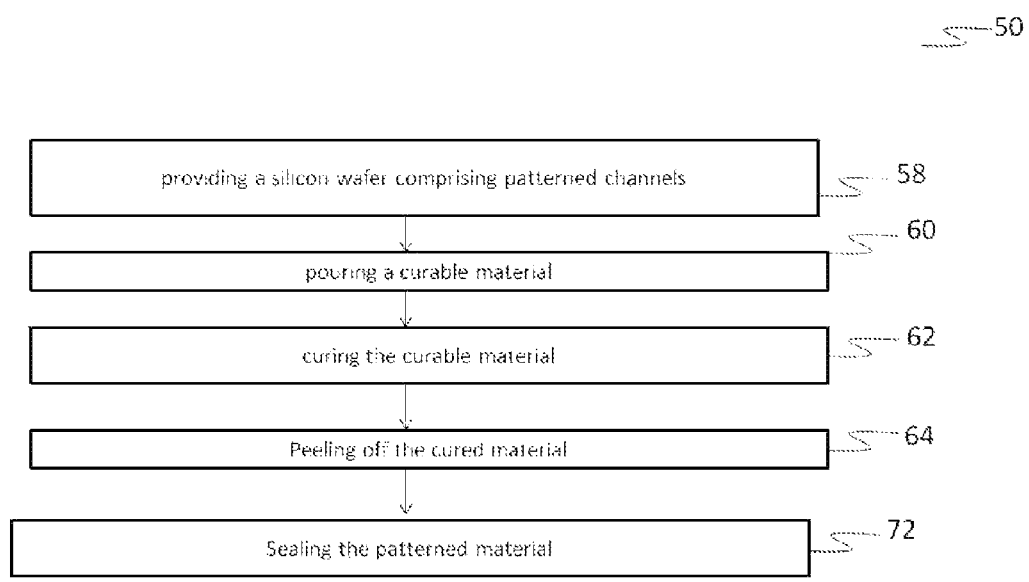
FIG. 9 is a flowchart representation of exemplary steps for a method for providing a shaped channel for making the diagnostic element.

One exemplary method for providing a shaped channel, depicted by numeral 50 in FIG. 7, is also shown in FIG. 9 and depicted by numeral 50, wherein the method comprises providing a silicon wafer 58 that comprises patterned channels. The silicon wafer comprising patterned channel may be bought from commercial sources as such, or may be created in a facile manner by the appropriate use of etching or photolithography using standard microfabrication techniques known in the art. An exemplary photolithography method involves the use of the photoresist material SU-8.

Then, the method comprises pouring a first curable material 60 on the silicon wafer containing positive features to form a curable channel in negative relief. Typical curable materials include those that may be cured upon exposure to high temperatures or a suitable radiation having a suitable wavelength. Some of the characteristics that may be used to select curable materials may include flowability of the curable material, curing time when exposed to curing conditions, nature of the cured material such as transparency, strength and the like. Some exemplary materials include, but not limited to, PDMS, polyurethane etc. In some embodiments, combination of materials may be used as the first curable materials.

The method for the formation of a shaped channel then involves curing the curable material as depicted by numeral 62 in FIG. 9. Curing may be effected by any suitable methods known in the art. Exemplary methods include heating, exposure to UV radiation, and the like. Curing results in the formation of a patterned material from the curable material. Subsequently the patterned material is peeled off from the silicon wafer, shown in FIG. 9 as numeral 64. The, the patterned material that is peeled off from the silicon wafer is sealed onto at least one surface, shown as numeral 72 in FIG. 9. In one exemplary embodiment, where the curable material is PDMS, curing may be effected by heating it for about 60 minutes, and after peeling it off from the silicon wafer, it is sealed reversibly by pressing on to a glass slide or irreversibly sealed to a glass slide by plasma-activated adhesion.

In another embodiment, the sealed channel is provided by injection molding an injection moldable or thermally embossable material, such as a thermoplastic material. Typical plastics that may be injection molded include, poly(m-ethyl methacrylate), poly(vinyl chloride), poly(methacrylate), polycarbonate, polyesters, polyimdies, cyclic olefin copolymer (COC) and the like. Such plastics are typically available from a variety of commercial sources. In one specific embodiment, the plastic useful in the invention is a poly(methyl methacrylate). The replicated plastic devices are then sealed to a flat sheet of similar plastic using an appropriate bonding process such as thermal bonding or adhesive activated bonding to provide a fully enclosed device.

Figure 10:
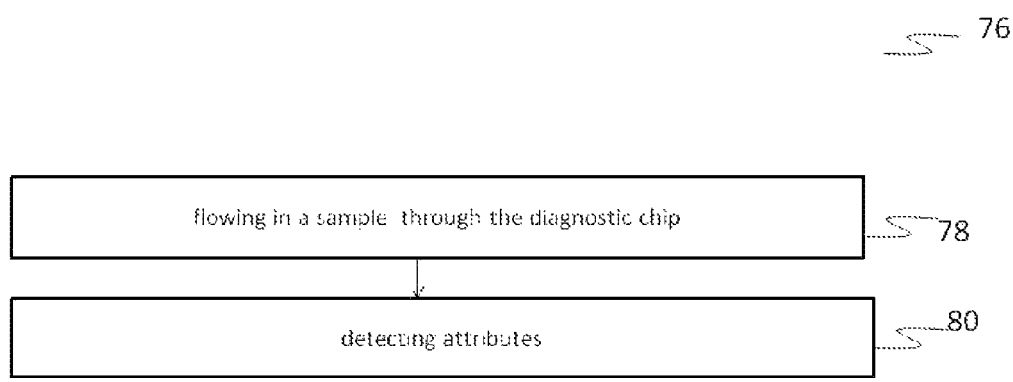
FIG. 10 is a flowchart representation of exemplary steps for a method for using the diagnostic element.

In another aspect, the invention provides a method for using a diagnostic element of the invention. This method is represented in a diagrammatic manner in FIG. 10, and is depicted by numeral 76. The method comprises flowing a sample 78 through the inlet passage into the diagnostic element that comprises the at least one diagnostic gel to provide an analyte diagnostic element. The analyte diagnostic element is then analyzed to detect attributes 80 associated with the analyte. The exact nature of the interaction between the diagnostic end of the diagnostic gel contained within the diagnostic device of the invention with an analyte is shown visually in FIGS. 3 and 4.

Figure 11:
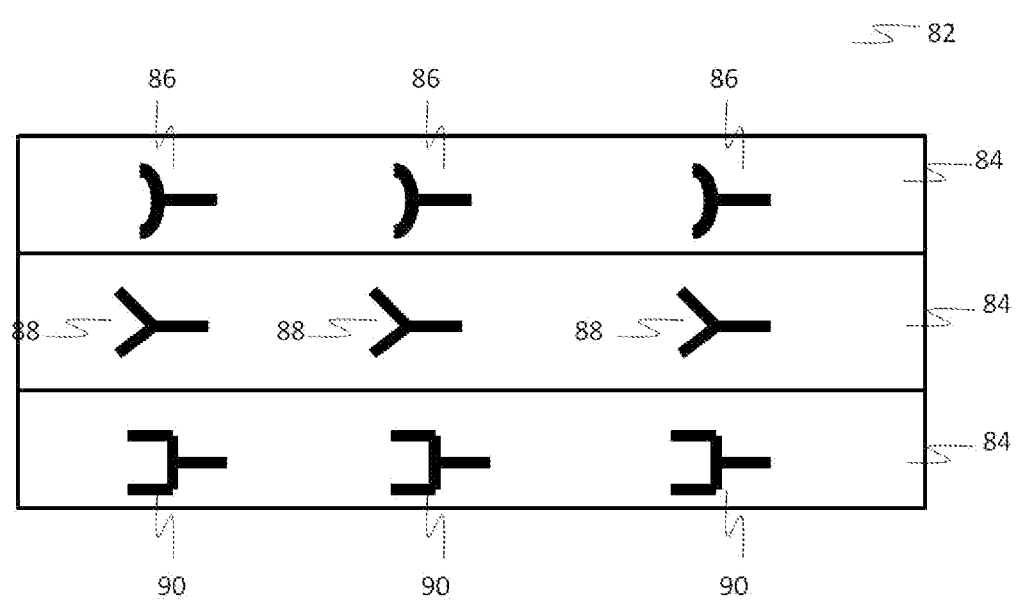
FIG. 11 is a diagrammatic representation of a diagnostic element for a multiplexed immunoassay according to an aspect of the invention.

In an exemplary embodiment illustrating the formation of a diagnostic element for a multiplexed immunoassay wherein the diagnostic element contains features as follows: Diagnostic element, shown in FIG. 11 and designated as numeral 82 containing three strips of hydrogel 84 is formed using a unique microfluidic methodology as described in US2007/105972A1. Briefly, the method involves using laminar flow to form spatially segregated strips of hydrogel 84, and then using UV photopolymerization through a shaped photomask to form a solid hydrogel with shape definition. Each strip of hydrogel 84 comprises a specific capture antibody 86, 88 and 90. In this exemplary embodiment, each strip of hydrogel is around 100 µm wide and a 200-330 µm long.

Figure 12:
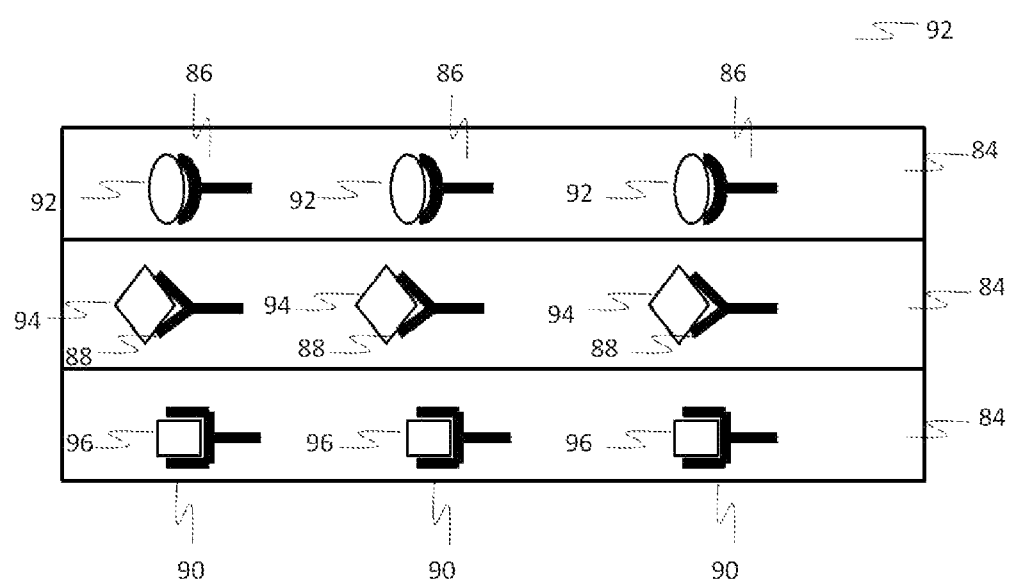
FIG. 12 is a diagrammatic representation of the diagnostic element of FIG. 10 with a plurality of analytes according to an aspect of the invention.
Figure 13:
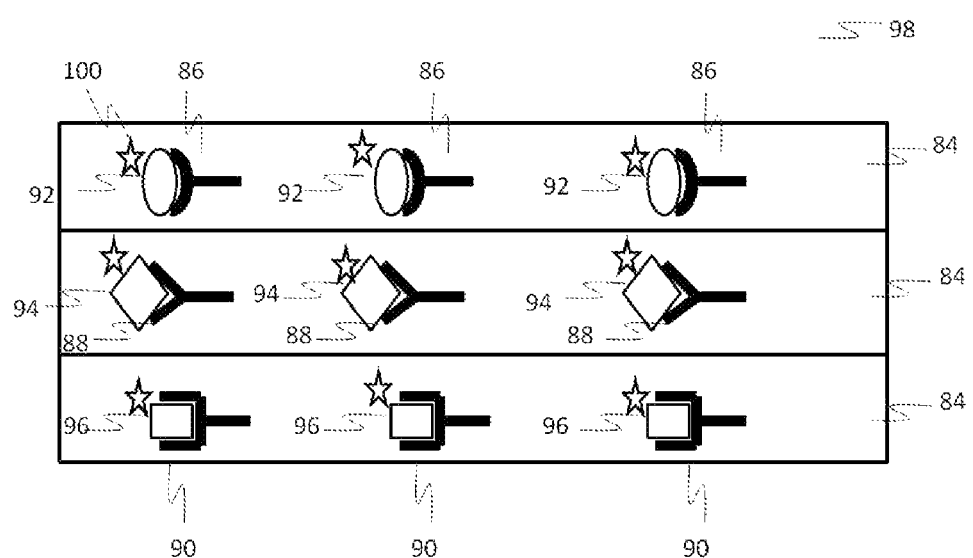
FIG. 13 is a diagrammatic representation of the diagnostic element of FIG. 11 with a fluorescently labeled secondary antibody according to an aspect of the invention.

FIG. 12 shows the use of the diagnostic element for a multiplexed immunoassay, depicted by numeral 92. Automated fluidic control is then used to supply a specific bodily fluid into the chip containing these hydrogel strips 84 which comprise the specific capture antibody 86, 88 and 90, which is then allowed to incubate for a predetermined time period. The time period required for the incubation will depend on the nature of antibodies and antigens, physical characteristics such as temperature, pressure, and the like, and can be easily determined by those skilled in the art. After incubation for a few minutes, antibodies 86, 88 and 90 bind themselves to specific antibodies, wherein the specific antibodies are depicted by numerals 92, 94 and 96 in FIG. 12. Subsequently, a washing step is performed to allow any unbound antigen to be washed away. FIG. 13 shows the preparation of the diagnostic element for an assay step, depicted by numeral 98. In this step, a fluorescently labeled secondary antibody depicted by numeral 100 in FIG. 13 is then flowed through the chip and incubated for a few minutes before unbound fluorescently labeled antibody is washed away. The fluorescently labeled secondary antibody is generally non-specific in its attachment and is capable of binding to any antigen or antibody in a given system. Alternately, fluorescently labeled secondary antibody may be capable of binding only to specific groups on specific antigens or antibodies. The fluorescent signal is then read from each of the lanes and the amount of each antigen present in the sample is deduced using the fluorescent signal.

The great advantage that this kind of assay system provides is that only a small volume of serum (~1 µl) is all that is required to perform the assay. Fluorescent signal sensitivity will depend on the detector used and can potentially be read down to the picomolar (10-12 M) level. The method has been shown here for only 3 strips, but may easily be extended to upto 10 proteins, and may even be extended to larger numbers by using an array of proteins as opposed to strips of them. The invention also solves the general problem of encapsulation and position of a given particle of interest within a particular area, which problem has been delineated by Becker et al. in Becker et al., Anal. Bioanal. Chem. (2008) 390: 89-111. The method of the invention may further be used as a technique for flowing in valves, electrodes, and for controlling the positioning suitable objects such as cells at a particular given area.

EXAMPLES

Hydrogel Formation

Figure 14:
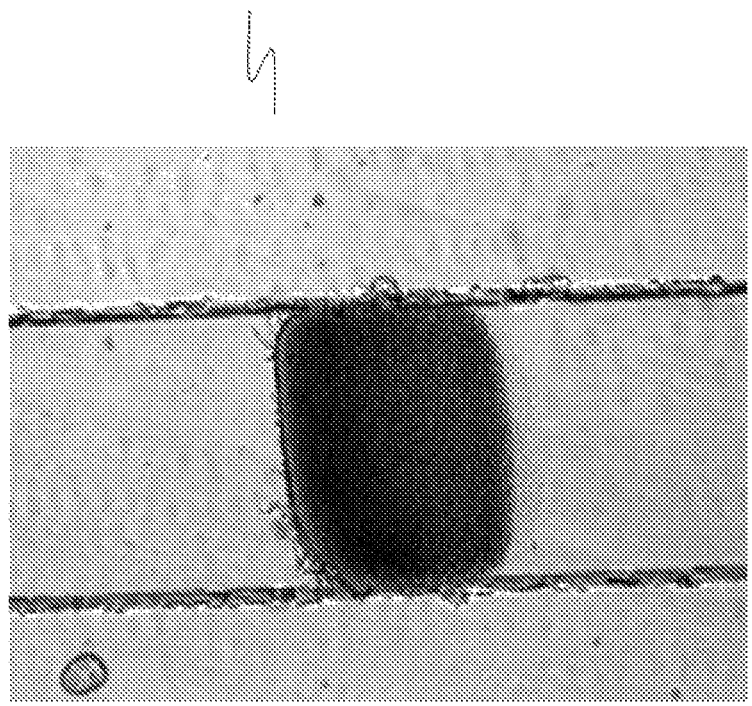
FIG. 14 is a photograph of the diagnostic gel of the invention.

A composition comprising the following components was used to form the diagnostic gel of the invention: 12.3 microliters (μl) of Polyethylene-diacrylate-700 (PEG-DA-700) from (Sigma Aldrich, 0.4 ul photoinitiator DAROCUR® 1173, 5 milligrams (mg) of $NaHCO_3$ (0.62M) and 87 μl of Phosphate Buffer Saline (PBS). Exposure conditions: ~10 seconds. Light intensities 25-100 $mW/cm^2$ of light. H=75 micrometer (pm). W=200-400 μm. Rectangular masks were used during exposure. The dimensions of the diagnostic gel of the invention were as follows: 300 μm length, 200 μm width and 75 μm thickness. FIG. 14 shows the photograph of the diagnostic gel of the invention, as depicted by numeral 102. The pores caused by the porogen are clearly visible herein.

In a comparative example, a composition comprising the following components was used to form a hydrogel: 12.3 μl of PEG-DA-700Sigma Aldrich, 0.4 μl DAROCUR® 1173photoinitiator, and 87 ul PBS was used to make the hydrogel. The dimensions of the hydogel made by the comparative example was similar to that of the diagnostic gel of the invention.

Figure 15:
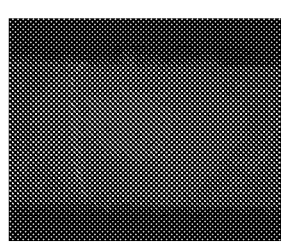
FIG. 15 is a fluorescent image of the diagnostic gel of the invention that has been treated with a fluorophore containing protein solution.
Figure 16:
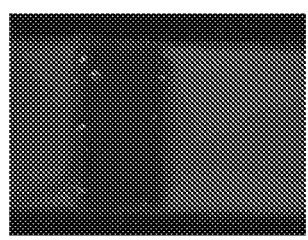
FIG. 16 is a fluorescent image of the hydrogel that has been treated with a fluorophore containing protein solution.

The diagnostic gel from the example and the hydrogel from the comparative example described herein was then treated with an 100 μg/ml aqueous solution of an antibody to insulin tagged with FITC, which is a fluorophore containing 150 kiloDalton protein. FIG. 15 shows the fluorescent image of the diagnostic gel that has been treated with the fluorophore containing protein solution, depicted by numeral 104. It can be seen that the fluorophore-containing protein was able to permeate through the porous diagnostic gel of the invention, thus obscuring the contours of the diagnostic gel. FIG. 16 shows the hydrogel of the comparative example treated with the fluorophore containing protein solution. The hydrogel depicted by numeral 106 shows that the protein is unable to permeate the hydrogel, as evidenced by the dark color of the gel.

The porous hydrogel of the example also showed the property of being able to 'squeeze' into the holding port at appropriate values of pressure/vacuum. The hydrogel as described in the comparative example, which was prepared without $NaHCO_3$ was rigid and unable to squeeze into the holding port as desired.

Device Fabrication

Devices were fabricated by pouring polydimethylsiloxane (PDMS, Sylgard® 184, Dow Corning) on a silicon wafer containing positive-relief channels patterned in SU-8 photoresist (Microchem). The thickness of the PDMS devices was always maintained to be 5 mm or greater. Devices were fabricated by cutting out the PDMS channel using a scalpel, punching a hole at one end using a biopsy punch to make inlet ports. The PDMS devices were then plasma sealed to glass slides spin-coated with PDMS after placing thin sacrificial layers of PDMS on the channel alone and on the region of the glass slide which sits right under the channel. This is to ensure that the oligomer was exposed only to non-plasma treated PDMS surfaces while ensuring that the device is still effectively sealed.

Photomasks containing the valve shapes were designed in AUTOCAD 2007 and printed using a high resolution printer from Fineline Imaging (Boulder, Colo.). Each mask was inserted into the field-stop of the microscope to be used for projection photolithography. A 100 W HBO mercury lamp served as the source of UV light. A filter set that provides wide UV excitation (11000v2: UV, Chroma) was used to select light of the desired wavelength and a VS25 shutter system (Uniblitz) driven by a computer controlled VCM-D1 shutter driver provided specified pulses of UV light. Typical exposure times used were 100-1000 milliseconds (ms) and pressures were between 0.1 and 1 pounds per square inch (psi). Devices were mounted on an inverted microscope (Ti-S, Nikon) and the formation of the gel structures was visualized using a CCD camera (Micropublisher 3.3 RTV, Qimaging).

Design and Fabrication of a Microfluidic Device:

The design of a microfluidic device is shown in FIG. 2. The microfluidic device has three inlets (for multiplexing of proteins) which combine to form a channel and a single outlet at the other end. The channel dimensions are 5000 μm length, 300 μm width and 75 μm height. The channel width is constricted at one end called as constriction zone or inlet passage to let the gel squeeze. The left side of the constriction is called gel formation zone or preparation port where antibodies are polymerized in a multiplexed fashion using laminar flow theory to form a porous hydrogel. The gel is squeezed through the constriction and trapped on the other side of the constriction called as trap zone or holding port. Three different devices with different width constriction were designed namely, 200 μm, 150μ and 100 μm. The width of the outlet channel is half of the width of the constriction zone channel i.e., 100 μm, 75 μm and 50 μm respectively.

The reagent encapsulation process required two steps—the first was hydrogel fabrication and the second was hydrogel trapping. Hydrogel structures were fabricated using the previously designed technique of stop-flow lithography. An important requirement for hydrogel trapping was that the structures fabricated were soft enough to squeeze through constrictions. In order to achieve this, macroporous hydrogel structures were fabricated using the technique described herein above. These structures show the necessary mechanical properties that allow them to flow through channel constrictions that are smaller than their unrestrained sizes.

Device Interfacing

Fluid flow through the microfluidic channel was controlled using both vacuum and pressure sources generated by a D771-11 BTC-IIS series micropump (Hargraves, USA). The source was connected to the microfluidic device through Tygon tubing and fluidic action was automated using miniaturized "Ten Millimeter" solenoid valves (Pneumadyne, USA) controlled by Labview software.

Detection

The detection of the fluorescent signal emanating from the hydrogel was measured using images captured by a Coolsnap EZ CCD camera (Photometrics, Singapore). The signal intensity from each strip was averaged using ImageJ software before being quantified. Noise filtering was done by subtracting the signal from a control strip that contained no primary antibody.

Effect of Pressure on Hydrogel Trapping

The hydrogel trapping relies on the premise that a certain minimum threshold pressure (Pmin) is required to squeeze the structure through a channel smaller than it in width. Further, once trapped, the particle can withstand a certain maximum pressure (Pmax) before it is squeezed out in the opposite direction. In the manufacturing process therefore, a pressure Pman is used where (Pmin<Pman<Pmax). During the assay, the pressure used (Peli) must be such that the particle does not squeeze out in the direction from which it entered and therefore we have Peli<Pmin. The threshold pressures described are functions of the mechanical properties of the hydrogel and the geometry of the channel structures. An equation describing the quantitative dependence of threshold pressure on these parameters can be derived based on knowledge and skill of the user, experience and historical data of the device.

In our experiment positive pressures were applied to the ports used for the flow of reagents which make up the hydrogel structure and vacuum was applied to the ports which are required to draw in the fabricated hydrogel structure. Pressure and vacuum were applied alternately using the computer controlled solenoid valves.

Effect of Number of Channels

The encapsulation scheme described can be extended to fabricate a large number of channels containing encapsulated hydrogel. The PDMS gasket was used in one example and was controlled by separate channels to which pressure or vacuum were applied as desired to close and open the gasket respectively. Pressure or vacuum were applied through miniature 3-way solenoid valves (Pneumadyne) and controlled using a program written in Labview™.

While only certain features of the invention have been illustrated and described herein, many modifications and changes will occur to those skilled in the art. It is, therefore, to be understood that the appended claims are intended to cover all such modifications and changes as fall within the true spirit of the invention.

REFERENCES

1. Becker, H. and C. Gärtner, *Polymer microfabrication technologies for microfluidic systems*. Analytical and Bioanalytical Chemistry, 2008. 390(1): p. 89-111.
2. Dendukuri, D., et al., *Continuous-flow lithography for high-throughput microparticle synthesis*. Nat Mater, 2006. 5(5): p. 365-369.

We claim:

1. A diagnostic gel composition having dimensions ranging from about 250 nanometers to about 1000 micrometers, and a Young's modulus ranging from about 10 kilopascals to about 200 kilopascals, wherein the diagnostic gel composition is derived from a compound having a formula D-Sp-Po;

wherein D is a diagnostic group;
Sp is a hydrophilic spacer group; and
Po is a polymerizable group.

2. The diagnostic gel composition of claim 1, wherein D is an antibody produced by the body against a surface antigen on viruses.
3. The diagnostic gel composition of claim 1, wherein Sp is a poly(ethylene glycol) based group.
4. The diagnostic gel composition of claim 1, wherein Po is a vinyl group.
5. The diagnostic gel composition of claim 1, further comprising pores having pore size ranging from about 5 nanometers to about 1000 nanometers.
6. The diagnostic gel composition of claim 1 Po is a vinyl group and Sp is a poly(ethylene glycol) based group.
7. A diagnostic element comprising the diagnostic gel composition of 1.
8. A diagnostic device comprising the diagnostic element of claim 6.
9. A method of making a diagnostic gel composition, the method comprising:
    providing a composition comprising a porogen, an initiator and a compound having a formula;

D-Sp-Po;

polymerizing the composition to form a polymerized composition;
    washing the polymerized composition to form the diagnostic gel composition;
    wherein D is a diagnostic group; Sp is a hydrophilic spacer group; and Po is a polymerizable group, and wherein the diagnostic gel composition has a Young's modulus ranging from about 10 kilopascals to about 200 kilopascals.
10. The method of claim 9, wherein the polymerizing is by photopolymerization.
11. The method of claim 10, wherein the polymerizing is effected through a photomask.
12. The method of claim 9, wherein the porogen is sodium bicarbonate.
13. The method of claim 9, wherein the initiator is a photoinitiator.
14. The method of claim 9, wherein D is an HIV-antibody specific to a particular antigen.
15. The method of claim 9, wherein D is an aptamer.
16. The method of claim 9, wherein D is an oligonucleotide.
17. The method of claim 9, wherein Sp is a poly(ethylene glycol) based group.
18. The method of claim 9, wherein Po is a vinyl group.
19. The method of claim 9, further comprising washing off the porogen.

* * * * *